US009629399B2

(12) United States Patent
Raanan

(10) Patent No.: US 9,629,399 B2
(45) Date of Patent: Apr. 25, 2017

(54) HIP PROTECTOR SYSTEM AND METHOD FOR HIP FRACTURE PREVENTION

(75) Inventor: Amatsia Raanan, Raanana (IL)

(73) Assignee: Hip Hope Technologies Ltd., Hod HaSharon (IL)

( * ) Notice: Subject to any disclaimer, the term of this patent is extended or adjusted under 35 U.S.C. 154(b) by 833 days.

(21) Appl. No.: 13/983,066

(22) PCT Filed: Jan. 25, 2012

(86) PCT No.: PCT/IL2012/000041
§ 371 (c)(1),
(2), (4) Date: Aug. 1, 2013

(87) PCT Pub. No.: WO2012/104833
PCT Pub. Date: Aug. 9, 2012

(65) Prior Publication Data
US 2013/0312168 A1 Nov. 28, 2013

Related U.S. Application Data

(60) Provisional application No. 61/438,984, filed on Feb. 3, 2011.

(51) Int. Cl.
*A41D 13/018* (2006.01)
*A41D 13/05* (2006.01)
(Continued)

(52) U.S. Cl.
CPC ....... *A41D 13/0506* (2013.01); *A41D 13/018* (2013.01); *A61B 5/1117* (2013.01);
(Continued)

(58) Field of Classification Search
CPC .......................... A41D 13/018; A41D 13/0506
(Continued)

(56) References Cited

U.S. PATENT DOCUMENTS 4,637,074 A 1/1987 Taheri
5,362,098 A * 11/1994 Guill .................... A41D 13/018
2/456
(Continued)

FOREIGN PATENT DOCUMENTS

JP H11 335911 12/1999
JP 2000027010 A 1/2000
(Continued)

OTHER PUBLICATIONS

Supplementary Search Report of European Patent Application EP 12 74 2205 mailed on Oct. 29, 2015.
(Continued)

*Primary Examiner* — Gloria Hale
(74) *Attorney, Agent, or Firm* — Dr. Hanan Farber Patent Agent Ltd.

(57) ABSTRACT

An active hip protector system and method for hip fracture prevention are introduced in order to overcome the shortcomings of existing methods of preventing hip fractures; namely: to provide effective impact protection and eliminate false fall alarms. The hip protector system comprises a belt-like pouch, worn over the user's waist, containing airbags which are inflated to a large size ensuring that the user's thighs will not hit the ground upon impact, once the system detects a fall. The pouch contains all of the necessary elements for fall detection and activating inflation of the airbags. Incorporation of distance measurement sensors and cross reference with acceleration and spatial orientation sensors enable reliable detection of impending collision with the ground. The pneumatic system, including the airbags, is carried within the pouch or, alternatively, can be placed in a location that is prone to falling.

15 Claims, 9 Drawing Sheets

(51) Int. Cl.
*A61B 5/00* (2006.01)
*A61B 5/11* (2006.01)
*G08B 21/04* (2006.01)

(52) U.S. Cl.
CPC .... *A61B 5/6831* (2013.01); *A61B 2562/0219* (2013.01); *G08B 21/0446* (2013.01)

(58) Field of Classification Search
USPC ..... 2/2.5, 455, 456, 465–467, 228, 267, 268
See application file for complete search history.

(56) References Cited

U.S. PATENT DOCUMENTS

| | | | |
|---|---|---|---|
| 5,500,952 A * | 3/1996 | Keyes | A41D 13/018 2/465 |
| 5,584,072 A | 12/1996 | Kim et al. | |
| 5,937,443 A * | 8/1999 | Kageyama | A41D 13/018 2/455 |
| 7,017,195 B2 * | 3/2006 | Buckman | A41D 13/018 2/455 |
| 7,172,049 B2 | 2/2007 | Uchiyama | |
| 2002/0078484 A1 * | 6/2002 | Ulert | A41D 13/018 2/22 |
| 2004/0183283 A1 | 9/2004 | Buckman et al. | |
| 2005/0067816 A1 * | 3/2005 | Buckman | A41D 13/018 280/730.1 |
| 2006/0049950 A1 | 3/2006 | Lockhart | |
| 2006/0175337 A1 | 8/2006 | Defosset | |
| 2006/0191277 A1 | 8/2006 | Defosset | |
| 2006/0288464 A1 | 12/2006 | Warden | |
| 2013/0081189 A1 * | 4/2013 | Chiang | F41H 1/02 2/2.5 |
| 2013/0312168 A1 * | 11/2013 | Raanan | A41D 13/0506 2/465 |

FOREIGN PATENT DOCUMENTS

| | | |
|---|---|---|
| JP | 2000317002 A | 11/2000 |
| JP | 2004284381 A | 10/2004 |
| JP | 2009174102 | 8/2009 |
| JP | 2010001806 A | 7/2010 |
| KR | 842427 | 6/2008 |
| WO | WO 97/11616 | 4/1997 |
| WO | WO 2005/110133 | 11/2005 |

OTHER PUBLICATIONS

International Search Report of Application No. PCT/IL2012/000041 mailed on Jun. 8, 2012.
Douglas P Kiel et al, Efficacy of a Hip Protector to Prevent Hip Fracture in Nursing Home Residents, JAMA; the Journal of the American Medical Association, vol. 298; pp. 412-422, 2007.
Parker MJ et al., Hip protectors for preventing hip fractures in older people, PubMed.gov, Jul. 2005.
Yvonne F Birks et al., Age and Ageing, British Geriatric Society entitled: Randomized controlled trial of hip protectors for the prevention of second hip fractures, vol. 32, No. 4, 2003.
Bagala Fabio, et al. "Evaluation of accelerometer-based fall detection algorithms on real-world falls." PloS one 7.5 (2012): e37062.
First Office Action, Japanese Patent Office, App No. 2013-552323, Jan. 26, 2016.

* cited by examiner

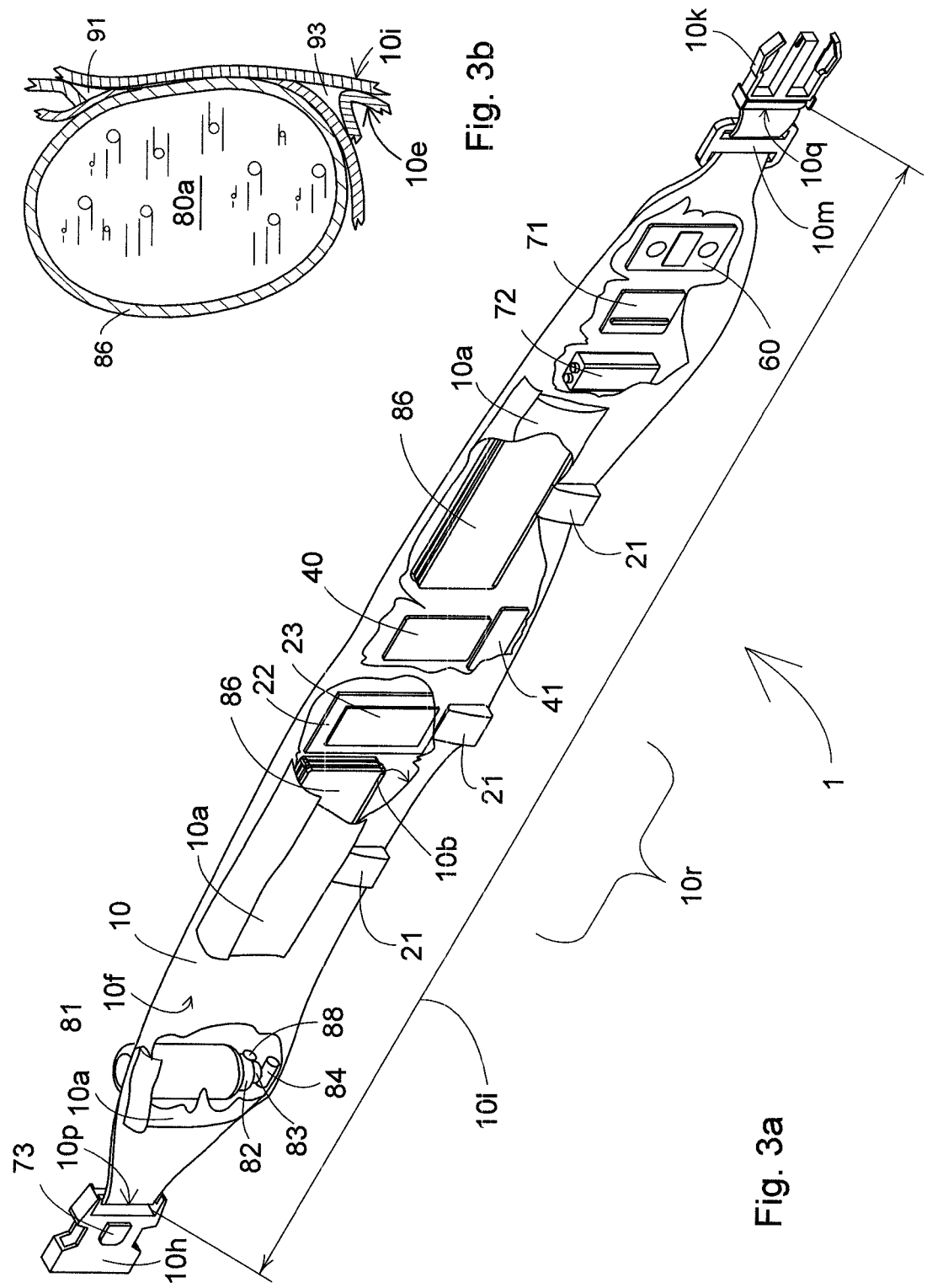

HIP PROTECTOR SYSTEM AND METHOD FOR HIP FRACTURE PREVENTION

REFERENCE TO CROSS-RELATED APPLICATION

This application is a National Phase Application of PCT International Application No. PCT/IL2012/000041, International Filing Date Jan. 25, 2012, entitled "HIP PROTECTOR SYSTEM AND METHOD FOR HIP FRACTURE PREVENTION", published on Aug. 9, 2012 as International Publication Number WO 2012/104833, claiming priority from U.S. Provisional Patent Application No. 61/438,984, filed Feb. 3, 2011, both of which are incorporated by reference in their entirety herein.

FIELD OF THE INVENTION

The present invention relates to hip protector systems, more particularly to active hip protector systems aimed at preventing hip fractures.

BACKGROUND OF THE INVENTION

Each year, millions of elderly people around the world (especially women) experience falls resulting in hip fractures (mainly, femoral neck fractures).

Hip fractures in the elderly result in physical suffering, loss of independence, a deteriorating mental state and high mortality rate.

Conventional hip protector devices are of a passive type. Typically, they comprise a hard high-density plastic shield and soft foam pads. These devices are usually inserted into especially designed pockets located over the hips, in undergarments, pants or belts.

Conventional passive hip protector devices have fundamental shortcomings especially:
  There is no unambiguous evidence as to their efficacy in preventing hip fractures
  Their cumbersome design and wearing result in low client compliance The following brief citations were taken from articles published in three professional magazines. The articles report on three independent clinical trials of conventional passive hip protectors carried out in The US and the UK.

Their conclusions demonstrate the above mentioned shortcomings:
  According to an article published in the professional magazine:
JAMA (the Journal of the American Medical Association), Douglas P. Kiel, MD, MPH et al., 2007; 298: 413-422, titled:
Efficacy of a Hip Protector to Prevent Hip Fracture in Nursing Home Residents:
Conclusions: In this clinical trial of an energy-absorbing/shunting hip protector conducted in US nursing homes, we were unable to detect a protective effect on the risk of hip fracture, despite good adherence to protocol. These results add to the increasing body of evidence that hip protectors, as currently designed, are not effective for preventing hip fracture among nursing home residents.
  According to an article published in the professional magazine:
PubMed.gov, Parker M J et al., (July 2005), titled:
Hip protectors for preventing hip fractures in older people:
  Authors' conclusions: Accumulating evidence casts some doubt on the effectiveness of the provision of hip protectors in reducing the incidence of hip fractures in older people. Acceptance and adherence by users of the protectors remain poor due to discomfort and practicality.
  According to an article published in the professional magazine:
Age and Ageing, Yvonne F. Birks, et al., 2003, vol. 32 no. 4. British Geriatric Society titled:
  Randomized controlled trial of hip protectors for the prevention of second hip fractures:
  Key Points
    The current evidence to support the use of hip protectors comes from residential care settings.
    This report describes the results of a secondary prevention trial in a community-based sample.
    No evidence for their efficacy in this sample.
    More work is required to test them in larger trials in both residential and community settings.

Several attempts to develop an active hip protector device were made, but none of them materialized into a viable solution.

This may be explained by two main reasons:
  Technical obstacle: A failure to implement a reliable fall detection method and logic that will avoid false alarms and faulty system activations.
  Compliance issue: A failure to design a comfortable wearable product that will be adopted by the elderly An example of such an attempt could be an active inflatable hip protector device described in U.S. Pat. No. 5,500,952 of Keyes, which is incorporated by reference for all purposes as if fully set forth herein.

The hip inflatable protection device contains motion sensors, an inflatable air bag folded into pleats, a battery, a gas cartridge, sensors to determine angular motion and acceleration, a triggering mechanism to release the gas and a relief valve.

When the user falls, the sensors automatically release gas from the cartridge and inflate the airbag assembly.

The motion sensors, according to Keyes, contain logic controlled circuits which do not permit inflation of the airbag assembly unless signals are received indicating both sufficient acceleration of the body and sufficient downward angular motion.

The sensors according to Keyes may include acceleration and orientation sensors.

When the hip inflatable protection device senses body movement of a selected and predetermined acceleration and senses downward angular motion of selected and predetermined magnitude, the device signals the triggering mechanism to fire. This releases compressed gas from the compressed gas cartridge inflating the invention.

After use the relief valve is opened to release air from the airbag assembly, the pleats are reinserted into the hip inflatable protection device, a gas cartridge is replaced and the hip inflatable protection device is ready for reuse.

The fact that, as of now, there is no effective solution to active real-time hip fracture prevention caused by falls is unambiguous.

Previous attempts to provide real-time active hip fracture prevention solutions lacked the capability to provide continuous measurement of the distance or height of the pelvis and the hips relative to the ground. Likewise, they lacked the combination of hip proximity to the ground data with pelvis vertical velocity and acceleration data in order to reliably detect falls.

Basing the assessment of a falling situation on angular diversion of the body could result in false activation, since as a person can regain balance after losing it, for example by means of grabbing a nearby piece of furniture. Namely, the solutions known today are not capable of properly and distinctly recognizing a situation of impending inevitable collision with the ground.

The invention described hereinafter is intended to solve the above mentioned deficiencies and suggest an innovative technical and device design approach.

By adding a robust height measurement system that will be placed on the body and cross referencing the height data with other sensors, the system will allow, for the first time, for significantly lower and acceptable false negative and false positive detection rates that will in turn enable the system to be put to real world usage.

BRIEF SUMMARY EMBODIMENTS OF THE INVENTION

The background art does not teach or suggest a system and/or a method that can properly recognize a situation of impending inevitable collision with the ground.

Embodiments of the present invention demonstrate a hip protector system that is intended to solve the above mentioned shortcomings of conventional hip protectors, by providing effective active real-time protection against hip fractures caused by falls.

Additional objects and advantages of the invention will be set forth in part in the description which follows and, in part, will be obvious from the description, or may be learned by practice of the invention.

According to the teaching of the present invention there is provided a hip protector system including: (a) a pouch having a pouch front cover, an external side, an internal side, a rear segment, a frontal segment, a left end, and a right end, wherein the pouch has a pouch length measured between the left end, and the right end, the pouch including: (i) at least one proximity sensor, located partially inside the pouch; (ii) at least one gyro, located inside the pouch; (iii) at least one accelerometer, located inside the pouch; and (iv) a micro controller unit located inside the pouch, wherein the micro controller unit is operatively connected to the proximity sensor, to the gyro, and to the accelerometer; and (b) a pneumatic sub-system, operatively connected to the micro controller unit, the pneumatic sub-system including: (i) a gas canister; (ii) a gas discharge valve attached to the gas canister, wherein the discharge valve is adapted to receive an inflation activation signal; (iii) a gas outlet attached to the discharge valve; (iv) a pneumatic tubule operatively connected to the gas outlet; (v) at least one gas valve operatively connected to the pneumatic tubule; (vi) at least one gas intake valve operatively connected to the pneumatic tubule; and (vii) at least one airbag operatively connected to the at least one gas intake valve.

According to the teaching of the present invention the pneumatic sub-system is located inside the pouch, the pouch further including; (viii) a main battery located inside the pouch, electrically connected to the at least one proximity sensor, the gyro, the accelerometer, the micro controller unit, and the gas discharge valve.

According to the teaching of the present invention the pouch further includes: (ix) a system status and integrity indicator, located inside the pouch, wherein the system status and integrity indicator is operatively connected to the micro controller unit, wherein the system status and integrity indicator is electrically connected to the main battery.

According to the teaching of the present invention the pouch further includes: (x) a power supply bus, located inside the pouch, electrically connected between the main battery and the at least one proximity sensor, between the main battery and the gyro, between the main battery and the accelerometer, between the main battery and the micro controller unit, between the main battery and the gas discharge valve, and between the main battery and the system status and integrity indicator.

According to the teaching of the present invention the system status and integrity indicator includes: (vii.i) a warning buzzer; (vii.ii) a fault display; and (vii.iii) a reset button.

According to the teaching of the present invention the pneumatic sub-system further includes: (v.vii) a manifold, operatively connected to the pneumatic tubule, between the gas outlet and the at least one gas intake valve; and (v.viii) a gas pressure gage attached to the gas canister, operatively connected to the micro controller unit, and electrically connected to the power supply bus.

According to the teaching of the present invention the pouch further includes:
(xi) an automatic alert/alarm transmitter, located inside the pouch, electrically connected to the main battery and operatively connected to the micro controller unit.

According to the teaching of the present invention the pouch further includes: (x) at least one compartment, wherein the at least one airbag is located inside the at least one compartment.

According to the teaching of the present invention the hip protector system further includes: (c) a locking device attached to the pouch.

According to the teaching of the present invention the hip protector system further includes: (c) a latch attached to the left end; (d) a buckle mounted on the pouch; (e) an adjustment clasp mounted on the pouch; and (f) an auto operation switch attached to the buckle, wherein the operation switch is electrically connected to the main battery, and operatively connected to the micro controller unit.

According to the teaching of the present invention the pouch further includes: (xi) a main switch, located inside the pouch wherein the main switch is electrically connected to the main battery.

According to the teaching of the present invention the at least one airbag is configured to have a predetermined airbag inflation size at a fully inflated state of the airbag.

According to the teaching of the present invention the pneumatic sub-system is located outside the pouch, wherein the pouch further includes: (vi) a main battery located inside the pouch, electrically connected to the at least one proximity sensor, the gyro, the accelerometer, and the micro controller unit; and (vii) a transmitter, located inside the pouch, electrically connected to the main battery and operatively connected to the micro controller unit.

According to the teaching of the present invention the pneumatic sub-system further includes: (viii) a gas pressure gage attached to the gas canister; (ix) a pneumatic sub-system switch; (x) a pneumatic sub-system battery electrically connected to the pneumatic sub-system switch, and to the gas discharge valve; and (xi) a receiver electrically connected to the pneumatic sub-system battery.

According to the teaching of the present invention the micro controller unit is adapted to continuously process distance signals received from the at least one proximity sensor, spatial orientation signals received from the gyro and vertical acceleration signals received from the accelerometer, and to control and to manage an automated operation of the hip protector system.

According to the teaching of the present invention the micro controller unit is adapted to continuously process distance signals received from the at least one proximity sensor, spatial orientation signals received from the gyro and vertical acceleration signals received from the accelerometer, and to control and to manage an automated operation of the hip protector system.

According to the teaching of the present invention the hip protector system further includes: (c) a decorative cover attached to the pouch.

According to the teaching of the present invention there is provided a method of operation of a hip protector system, the method including the stages of: (a) receiving a vertical acceleration signals from an accelerometer; (b) asking if the vertical acceleration is not equal to the gravity acceleration; (c) switching to idle mode of operation, if specific combinations of conditions in which both hip height data and the vertical acceleration data indicate a continuous motionless sitting or lying down situation; (d) switching to normal mode of operation as soon as the vertical acceleration value other than gravity acceleration value is identified; (e) receiving proximity measurement distance signals, from at least one proximity sensor and receiving spatial orientation signals provided by a gyro; (f) calculating height values based on the proximity measurement distance signals and the spatial orientation signals and transferring the height values to a height comparator; (g) determining a specific reference height value, once the wearer is in a fully stretched standing position; (h) computing downward velocity; (i) calculating height changes; (j) asking if a rate of change is continuous; (k) switching to end non-action mode, if the rate of change is not continuous; (l) asking if data values are within a collision envelope; (m) declaring an emergency fall detection status if a predetermined number of the within collision envelope data sets are found by a counter and fall trend analyzer.

According to the teaching of the present invention the method of operation of a hip protector system further includes the stages of (n) asking if to activate inflation, and if the answer is positive, sending an inflation activation signal; and (o) inflating at least one airbag.

According to the teaching of the present invention the method of operation of a hip protector system further includes the stages of: (p) discharging gas from the airbag; (q) reporting; and (r) turning the hip protector system to off mode.

According to the teaching of the present invention there is provided a method for use of a hip protector system, the method including the stages of: (a) wearing a pouch of a hip protector system by a wearer, around the wearer waist and adjusting the pouch to the wearer waist size by using an adjustment clasp; (b) locking a pouch locking device while a main switch is in on position, and automatically activating the hip protector system by an auto operation switch located in the locking device; (c) performing, by the hip protector system, a system auto-self-testing procedure; (d) issuing, by a buzzer of the hip protector system, a specific readiness confirmation sound and entering the hip protector system to a default normal mode of operation; and (e) as soon as the wearer is in a fully stretched standing position, the hip protector system is performing an automatic procedure of waist height re-calibrating.

According to the teaching of the present invention the method for use of a hip protector system further includes the stages of: (f) switching the hip protector system to an operating idle mode; and (g) switching the hip protector system to an operating normal mode.

According to the teaching of the present invention the method for use of a hip protector system further includes the stages of: (f) as soon as the hip protector system identifies an increased likelihood of an impending fall the hip protector system is automatically switching to fall alert mode of operation; (g) following an undoubted identification of a fall progression of the wearer that is going to end-up in a collision with a ground surface, the hip protector system is declaring an emergency fall detection situation and performing a series of automated operations intended to minimize impact damage and informing relevant people and authorities on the wearer's fall event; (h) issuing, by the hip protector system, a prompt command to inflate airbags in order to provide effective protection against fall impact and prevent the wearer hips from direct impact with the ground surface; and (i) inflating and popping out of the airbags.

According to the teaching of the present invention the method for use of a hip protector system further includes the stages of: (j) transmitting, by the hip protector system, an automated fall-alarm call/message; and (k) as soon as the airbags undergo a contraction caused by an impact with the ground surface an airbag gas discharge mechanism is automatically performing a controlled gas discharging process.

According to the teaching of the present invention the method for use of a hip protector system further includes the stage of: (l) after a predetermined time following the stage of inflating and popping out of said airbags, turning off the hip protector system.

BRIEF DESCRIPTION OF THE DRAWINGS

The invention is herein described, by way of example only, with reference to the accompanying drawings, wherein:

FIG. 3a is a perspective front view schematic illustration of an embodiment of a hip protector system according to the present invention.

FIG. 3b is a side cross section view through an airbag schematic illustration of an embodiment of a hip protector system according to the present invention.

Figure 1:
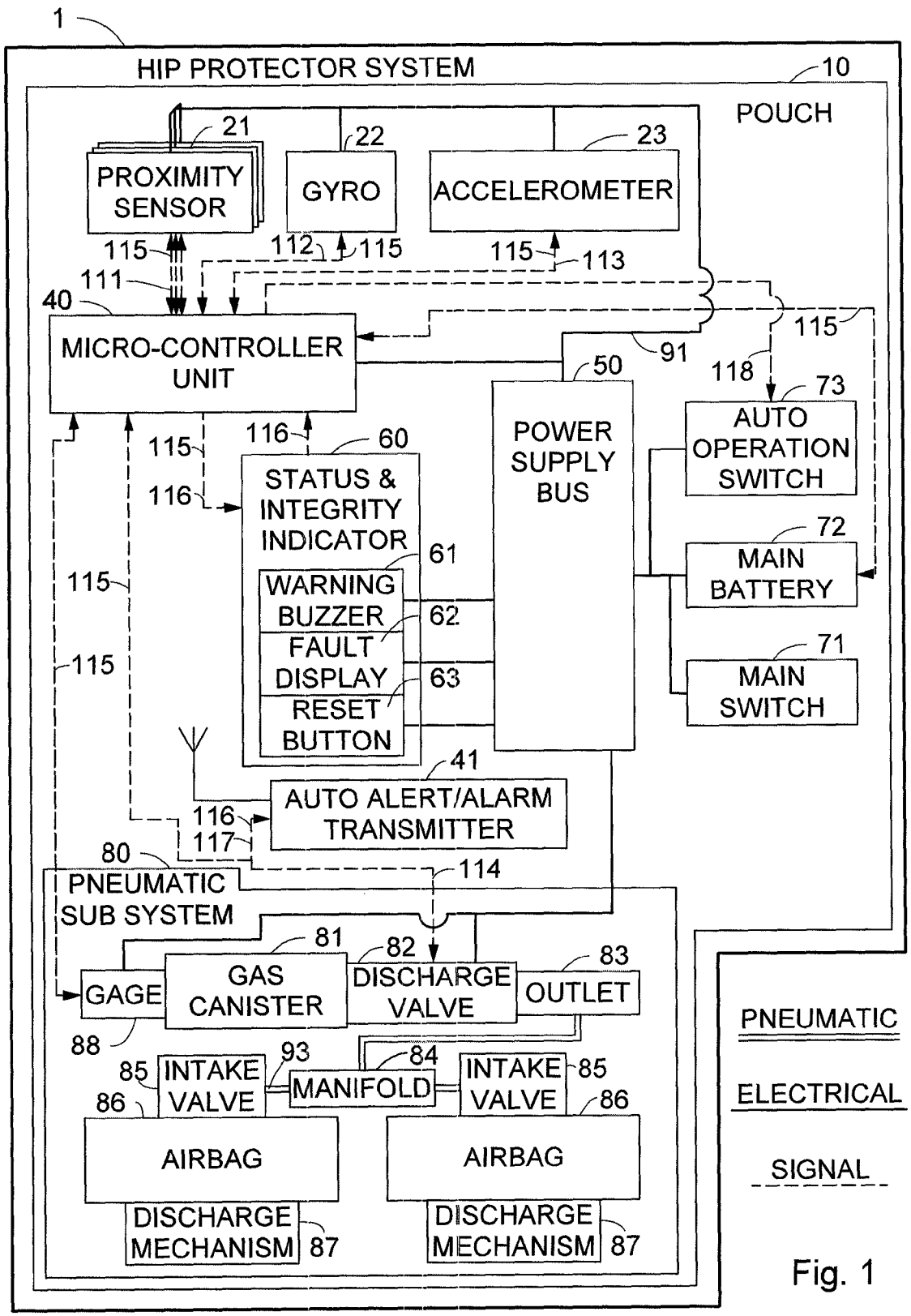
FIG. 1 is a schematic block diagram of an embodiment of a hip protector system according to the present invention.

In order to leave no room for doubt, the elements are shown in the illustrations of the present patent application in a manner that enables understanding them clearly, and the scales, size relations, and shapes are not in any way limiting their embodiment.

Likewise, it is noted that reference numerals may be repeated among the figures to indicate corresponding or analogous elements.

DETAILED DESCRIPTION OF EMBODIMENTS OF THE INVENTION

To remove any doubt, note that the manner in which the elements of the present invention are described in the illustrations can be highly detailed, however is not in any way limiting the present illustration, however is for the purpose of clarification and furthering understanding. The present invention can be implemented in embodiments that differ from the specification given with regard to the illustration.

The present invention is in the technical field of individual healthcare and safety.

More particularly, the present invention is in the technical field of hip protector systems aimed at preventing hip fractures as well as other fall related fractures that could result from fall impact of the pelvis with the ground.

The principles and operation of a hip protector system according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings.

Unless otherwise defined, all technical and scientific terms used herein have the same meaning as commonly understood by one of ordinary skill in the art to which this invention belongs. The materials, dimensions, methods, and examples provided herein are illustrative only and are not intended to be limiting.

The following list is a legend of the numbering of the application illustrations:

1 hip protector system
10 pouch
10a compartment
10b pouch front cover
10e external side (of the pouch)
10i internal side (of the pouch)
10r rear segment (of the pouch)
10f frontal segment (of the pouch)
10g locking device
10h buckle (of the locking device)
10k latch (of the locking device)
10m adjustment clasp
10l pouch length
10p left end (of the pouch)
10q right end (of the pouch)
12 decorative cover
12a hook-and-loop fasteners
21 proximity sensor
21a proximity sensor tilt angle
21b the proximity sensor package downward axis
21c a line perpendicular to the plane of wearer's waist
22 gyro
23 accelerometer
40 MCU (Micro Controller Unit)
41 automatic alert/alarm transmitter
50 power supply bus
60 system status and integrity indicator
61 warning buzzer
62 fault display
63 reset button
71 main switch
72 main battery
73 auto operation switch
74 pneumatic sub-system battery
75 pneumatic sub-system switch
80 pneumatic sub-system
80a gas
81 gas canister
82 gas discharge valve
83 gas outlet
84 manifold
85 gas intake valve
86 airbag
87 gas discharge mechanism
88 gas pressure gage
91 electrical wire
92 signal line
93 pneumatic tubule
101 hip to ground surface distance
102 height
102a shortest height
102b reference height
103 downward velocity
104 comparison and calculation
105 gas discharge
106 reporting
107 vertical acceleration
108 height calculator
109 height comparator
110 commanding to turn the system off
111 distance signal
112 spatial orientation signal
113 vertical acceleration signal
114 inflation activation signal
115 self-test activation signal
116 system malfunction alert signal
117 fall-alarm activation signal
118 system turn-off signal
120 airbag inflation size
122 pelvis to ground surface distance
200 wearer
201 waist (of the wearer)
202 hip (of the wearer)
203 pelvis (of the wearer)
204 wearer's waist plane
205 abdomen (of the wearer)
250 ground surface
260 object (on the ground)
301 storage device containing height sampling database
302 storage device containing collision envelope database
303 storage device containing continuity criteria and scenarios
304 storage device containing downward velocity database
401 asking: "vertical acceleration other than gravity?"
402 asking: "continuous rate of change?"
403 asking: "within collision envelope?"
404 asking: "activate inflation?"
410 counter and fall trend analyzer
450 end
501 transmitter
502 receiver
601 normal mode

602 idle mode
603 fall alert mode
604 fall detection mode

Embodiments of the present invention disclose an active hip protector system equipped with a fall detection capability, based (among other elements and characteristics) on proximity sensing. The hip protector system provides active protection against hip fractures caused by falls.

Hereinafter, embodiments of the present invention are explained in detail by referring to the drawings.

FIG. 1 is a schematic block diagram of an embodiment of a hip protector system 1 according to the present invention.

Components of the hip protector system 1 are engaged in a belt-like pouch 10 made of, for example, fabric. The illustration shows that electrical currents flow between the components of the hip protector system 1 through electrical wires 91 and power supply bus 50. Signals are transmitted through signal lines 92, and the gas flows through pneumatic tubule 93, however this is in no way limiting the present invention.

In case of a fall event, the inflated airbags 86, made for example from fabric or thermoplastic material, provide the essential physical protection to the hips of the wearer by cushioning, absorbing, and dissipating the fall impact energy and preventing direct contact between the hips and the ground surface.

The hip protector system 1 includes a pneumatic subsystem 80, which may also include gas canister 81, which is connected to a gas pressure gage 88 and a gas discharge valve 82, which is connected to a gas outlet 83. The gas outlet 83 is connected to a pneumatic tubule 93, which is split by means of a manifold 84, from which a pneumatic tubule 93 goes to each gas intake valve 85 of each one of the airbags 86.

Note that other configurations of pneumatic systems are also included in the scope of the present invention.

Figure 3C:
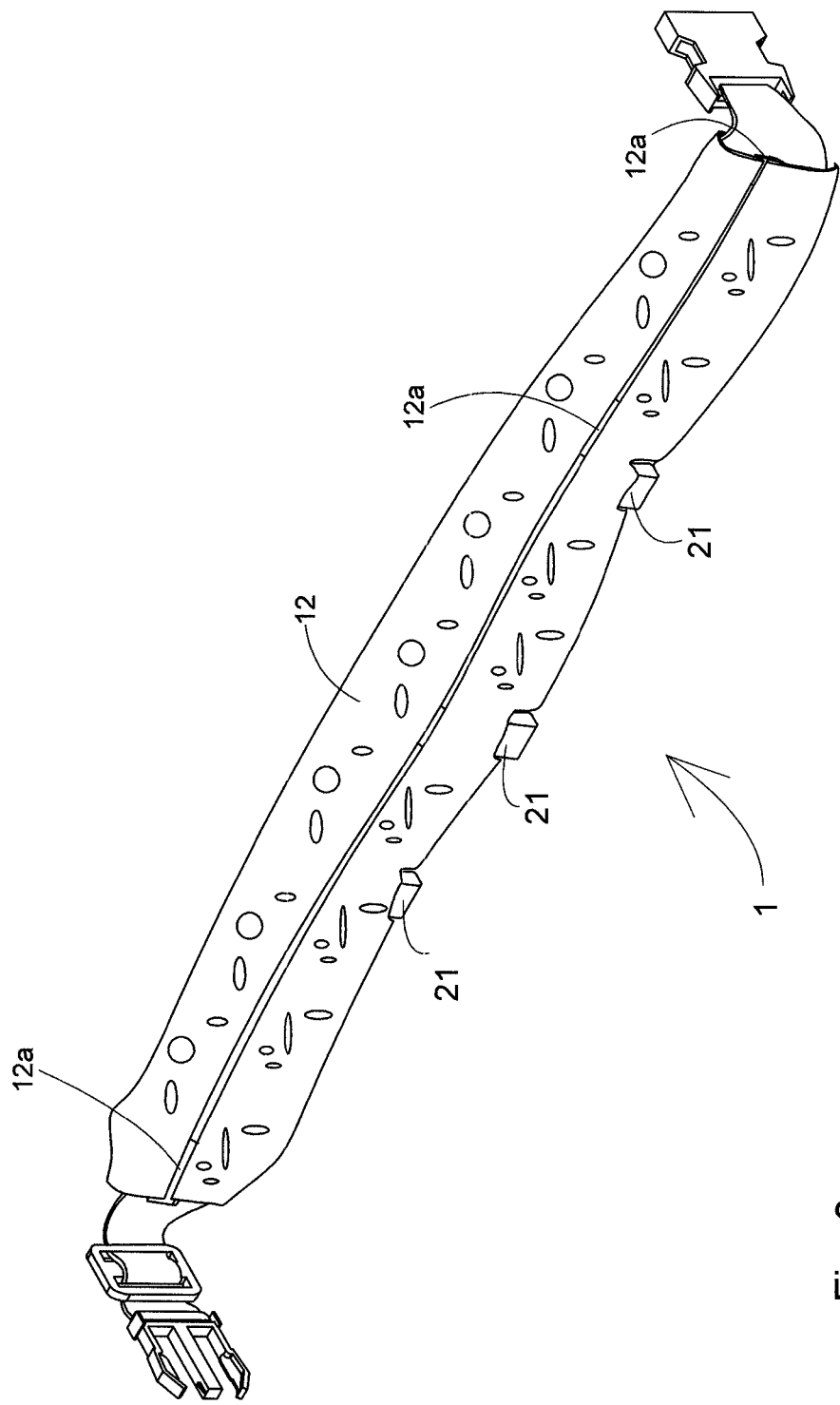
FIG. 3c is a perspective back view schematic illustration of an embodiment of a hip protector system 1 ornamented with a decorative cover 12 according to the present invention.
Figure 4:
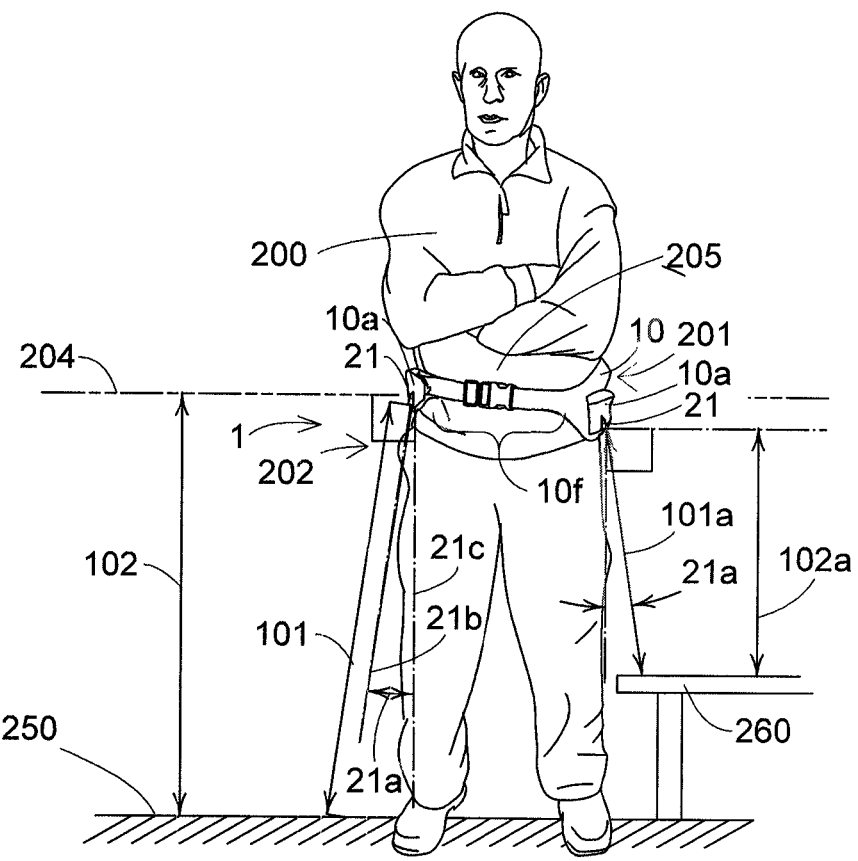
FIG. 4 illustrates a wearer standing while wearing a hip protector system according to the present invention, the airbags of which are not inflated.
Figure 5:
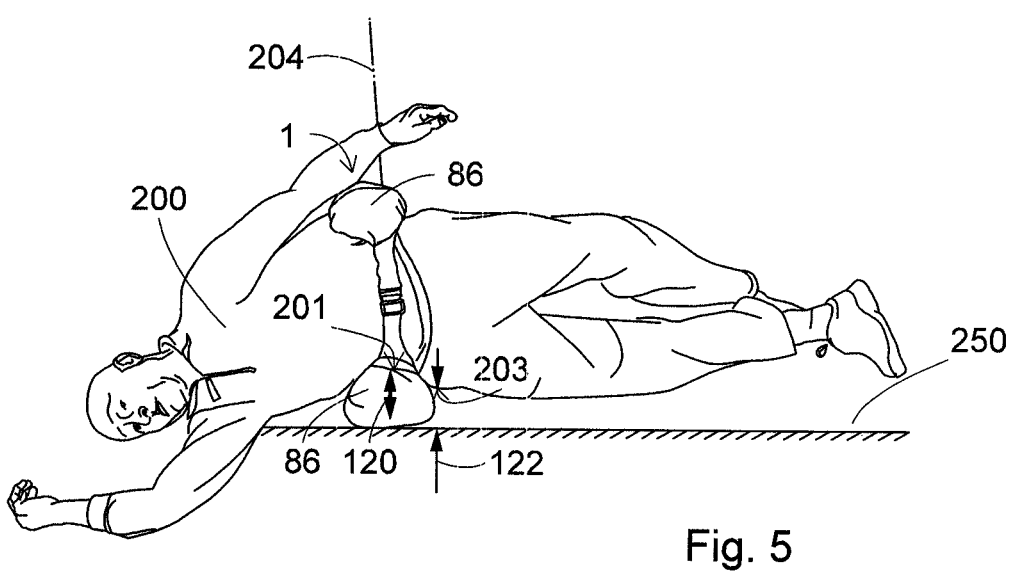
FIG. 5 illustrates a wearer lying on the side after having fallen, wearing a hip protector system according to the present invention, the airbags of which are inflated.
Figure 7:
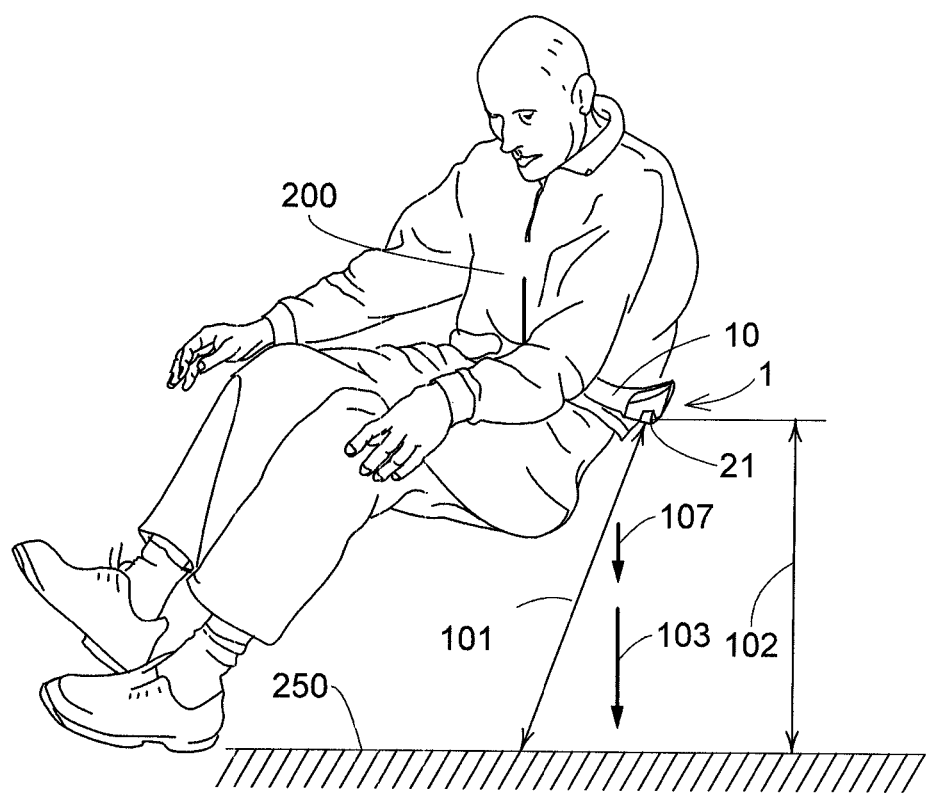
FIG. 7 illustrates a wearer, in mid-fall situation, wearing a hip protector system according to the present invention.

In order to achieve a better cushioning effect, according to one variation of the embodiment, the airbags 86 are equipped with a gas discharge mechanism 87 that releases part of the gas 80$a$ (not shown in the present drawing, shown in FIG. 3$b$), following the airbag 86 contraction caused by impact with the ground surface 250, (not shown in the present drawing, shown in FIGS. 4, 5 and 7).

One or more gas canisters 81 contain compressed gas 80$a$ required for airbag 86 inflation.

The gas 80$a$ could be for example helium, nitrogen, $CO_2$ or any other suitable gas. The overall volume of the gas canister/s could be for example 0.05 liter. The overall volume of the released gas could be for example 16 liters, divided equally between the two airbags. The size of the fully inflated airbag could reach for example 30 cm parallel to the waist plane 204 of the wearer.

The gas 80$a$ is released into the airbags 86, for example using inlaid pneumatic tubules 93.

Once the gas discharge valve 82 receives an activation signal from the system's MCU (Micro Controller Unit) 40, it immediately triggers for example an electro-mechanic sequence of operation by which the gas canister 81 discharges its content through the gas outlet 83.

According to a variation of the embodiment, electrical wiring that includes wires 91 connects all electricity consuming components to the main battery 72 via a power supply bus 50.

According to a variation of the embodiment an auto operation switch 73 is electrically connected to the power supply bus 50.

According to a variation of the embodiment an auto alert/alarm transmitter 41 can receive signals from the MCU 40.

Figure 6:
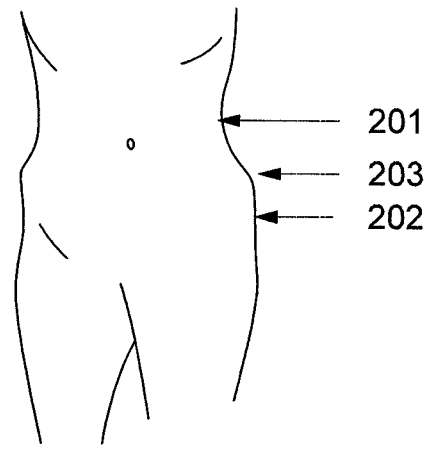
FIG. 6 illustrates the location of the waist, the hip, and the pelvis in the human body.

According to a variation of the embodiment, a proximity sensor 21, of ultrasonic type, or infrared type, or laser diode coupled with Complementary Metal Oxide Semiconductor (CMOS), or Charge Coupled Device (CCD) image sensors or laser diode coupled with a time of flight detector, is positioned, for example, adjacent to each hip 202 (not shown in the present drawing, shown in FIGS. 5 and 6), and a third proximity sensor 21 is positioned adjacent to the rear center of the pelvis 203 (not shown in the present drawing, shown in FIG. 6).

Each proximity sensor 21 provides measurements of hip to ground surface distance 101 from the hip 202 or the pelvis 203 to the ground surface 250 (not shown in the present drawing shown in FIGS. 4, 5 and 6), which according to a variation of the embodiment are performed on a continuous data sampling basis.

The fall detection method and logic of operation enable the hip protector system 1 to distinguish between measurements of the distance to the ground surface and the distance to other objects that may reflect the transmitted signals.

This unique capability of the hip protector system 1 is achieved through the fusion and analysis of the signals received from both the proximity sensors 21 and the gyro-accelerometer sensor (or gyro 22 and accelerometer 23 sensors).

MCU 40 controls and manages an automated operation of the hip protector system 1 by receiving, processing, calculating, updating and storing data and by receiving and sending signals from and to the system modules and components.

The MCU 40 processes input signals received from the fall sensing sensors such as proximity sensors 21, gyro 22 and accelerometer 23.

According to a variation of the embodiment the gyro 22 and accelerometer 23 are applied in a single package by means of MEMS technology.

The present invention is not limited to the usage of any specific quantity of any type of sensor.

According to a variation of the embodiment, a gyro 22 is located adjacent to the center of the rear segment 10$r$ (not shown in the present drawing, shown in FIG. 3$a$) of the pouch 10 and may provide the MCU 40 with information on the spatial orientation of the wearer's waist plane 204 (not shown in the present drawing, shown in FIGS. 4 and 5).

According to a variation of the embodiment an accelerometer 23 located adjacent to the center of the rear segment 10$r$ of the pouch provides the MCU 40 with the data required for the computation of the wearer's pelvis 203 (not shown in the present drawing, shown in FIGS. 5 and 6) vertical acceleration.

The rear segment 10$r$ of the pouch 10 is defined as a segment designated to be in close proximity to the back of the wearer when he or she is wearing the hip protector system 1.

According to a variation of the embodiment an automatic alert/alarm transmitter 41 may for example send an alarm by means of voice calls and/or text messages to pre-selected phone numbers, notifying them of the fall event of the system wearer immediately following airbag deployment. The voice/text messages may be sent for example via an application installed in the wearer's cellular phone.

The frontal segment 10$f$ (not shown in the present drawing, shown in FIGS. 3$a$ and 4) of the pouch 10 is defined as a segment designated to be in close proximity to the user's abdomen 205 (not shown in the present drawing, shown in FIG. 4) when he or she is wearing the hip protector system 1.

According to a variation of the embodiment a system status and integrity indicator 60 may be located in the frontal segment 10*r* of the pouch 10.

The system status and integrity indicator 60 can also include, for example, as shown in the illustration, warning buzzer 61, fault display 62, and reset button 63, however these are in no way limiting the present invention and the system status and integrity indicator 60 may provide for example visual and audio indications on battery level, gas pressure level, sensor intactness, wiring integrity, alarm system intactness and more.

According to a variation of the embodiment, in order to ensure the physical and functional integrity of the system, the MCU 40 may perform automatic self-test procedures, during which for example the aforementioned system parameters are checked on a continuous basis or otherwise.

Following the detection of a malfunction, the MCU 40 issues an alert, such as a warning sound of the buzzer 61 and/or a visual alert to the wearer.

An electricity source, such as a rechargeable main battery 72, provides power to the hip protector system's electricity consuming modules, through a power supply bus 50.

According to a variation of the embodiment the main switch 71 is formed and operated so as to avoid unintentional shut down, for example by means of a socket protected turn-off mechanism.

Figure 2A:
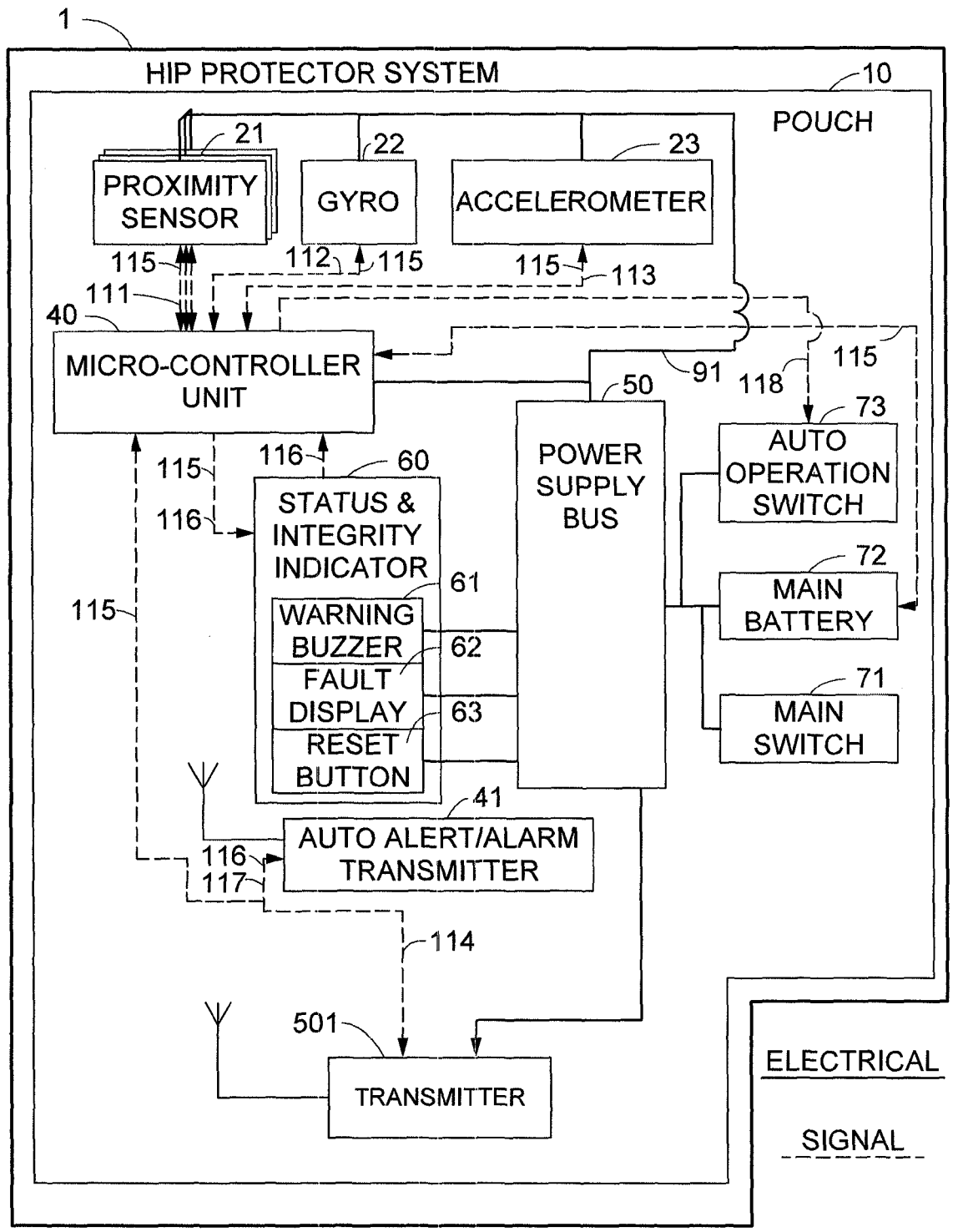
FIG. 2a is a schematic block diagram of an embodiment of a split hip protector system, without a pneumatic sub-system, according to the present invention.

FIG. 2*a* is a schematic block diagram of an embodiment of a split hip protector system 1, without a pneumatic sub-system 80, according to the present invention.

According to the present embodiment, the airbag 86 or airbags 86 (not shown in the present drawing, shown in FIGS. 1, 2*b*, 3*a*, 3*b* and 5) are not carried within the pouch 10, but rather are positioned elsewhere in the wearer's close vicinity. This can be on the wearer 200 (not shown in the present drawing, shown in FIGS. 4, 5, and 7), or in a stationary or mobile position, such as on the floor or the walls or other objects located in a room of a house or inside a bath or a shower.

According to the present embodiment, communication with the pneumatic sub-system 80 (not shown in the present drawing, shown in FIGS. 1 and 2*b*) could be achieved via Wi-Fi, Bluetooth or another form of short-range communication protocol, and in this case the pouch 10 contains a suitable transmitter 501.

Figure 2B:
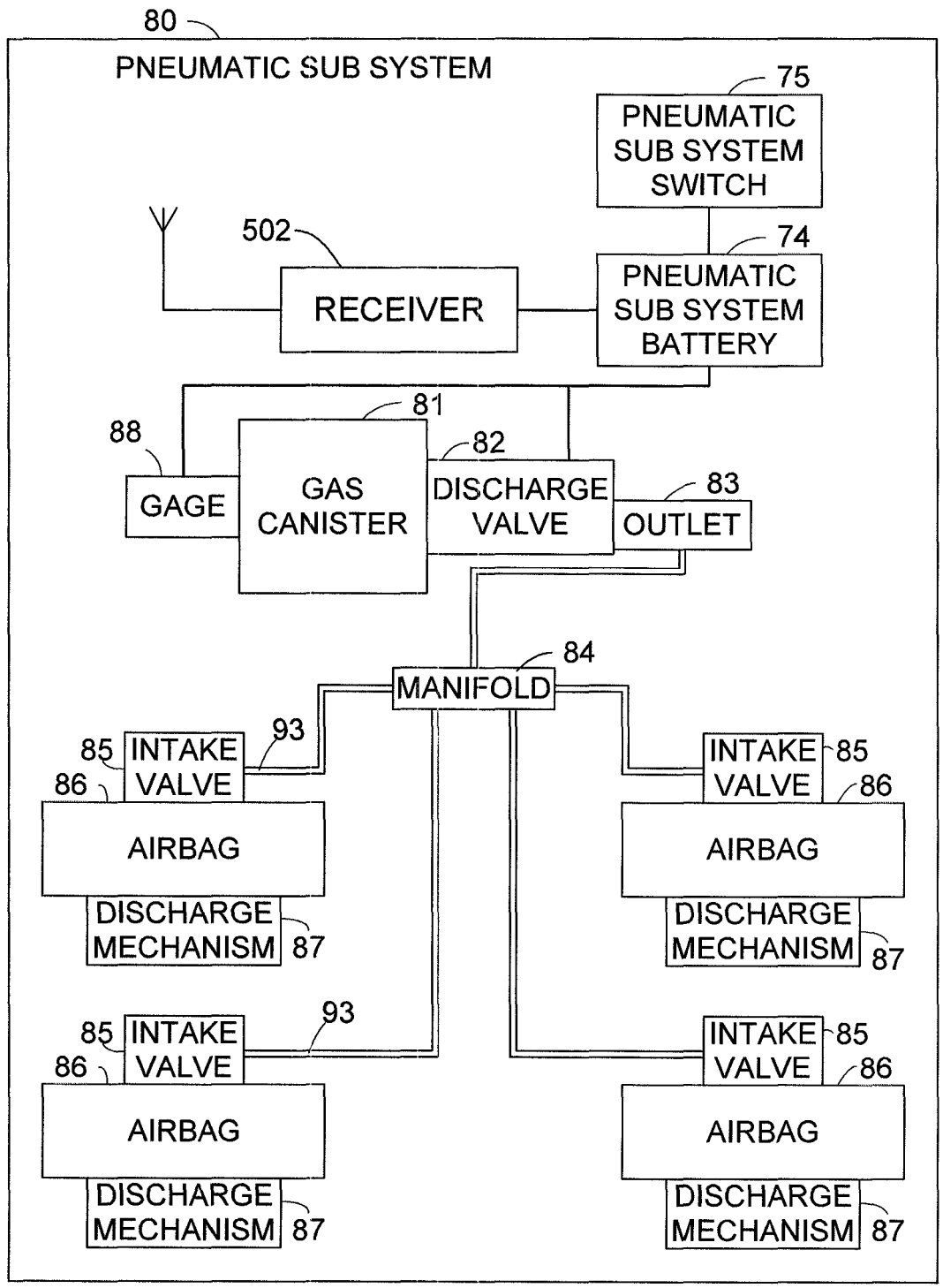
FIG. 2b is a schematic block diagram of an embodiment of a pneumatic sub-system, according to the present invention.

FIG. 2*b* is a schematic block diagram of an embodiment of a pneumatic sub-system 80, according to the present invention.

The pneumatic sub-system 80 according to the present embodiment can also be positioned elsewhere in the wearer's close vicinity, in a stationary or mobile position, such as on the floor or the walls or other objects located in a house room or inside a bath or a shower.

In this case, the pneumatic sub-system 80 is activated via Wi-Fi, Bluetooth, or another form of short-range communication protocol, by transmission received from transmitter 501 (not shown in the present drawing, shown in FIG. 2*a*).

The pneumatic sub-system 80 includes a receiver 502 and receives electric energy from a pneumatic sub-system battery 74 which can be activated and deactivated by means of a pneumatic sub-system switch 75.

The present illustration shows four airbags 86, however this is in no way limiting the present invention and there may be a different quantity in use. Likewise, the shape and size of the airbags 86 and their volume in an inflated state can be varied. Likewise, the volume of the gas canister 81 should to conform the overall volume to which the compressed gas within is supposed to expand.

FIG. 3*a* is a perspective front view schematic illustration of an embodiment of a hip protector system 1 according to the present invention.

To enable presentation of the components contained within the pouch 10, in several places, pieces of the pouch front cover 10*b* have been removed from the illustration.

During usage, the pouch 10 is worn around the waist 201 of the wearer 200 (not shown in the present drawing (shown in FIGS. 4, 5, and 7) and locked by a locking device such as a quick release buckle 10*h* and latch 10*k* comprising a locking device 10*g*.

The buckle 10*h* is described here as connected to the left end of the pouch 10*p* and the latch 10*k* is described here as connected to the right end (of the pouch) 10*q*. Likewise, an adjustment clasp 10*m*, designated to enable adjusting the size of the pouch length 10*l*, is assembled for the purpose of strapping onto the waist 201 of a specific wearer 200.

The illustration shows auto operation switch 73, which is assembled to the buckle 10*h*.

After strapping on the pouch and locking the locking device 10*g*, when the latch 10*k* is engaged with the buckle 10*h*, the auto operation switch 73 is activated and triggers the hip protector system 1 by enabling the connection of the main battery 72 to the electricity consuming components through the power supply bus 50.

The pouch 10 incorporates compartments 10*a* designed for storing the system components.

Inflatable airbags 86 are stored in external compartments 10*a*, at least one of which, according to one variation of the embodiment, is an external side quick-opening compartment 10*a*.

Once inflated, the airbags 86 instantly pop out of their compartments 10*a* while staying attached to the pouch 10.

In case of a fall event, the inflated airbags 86 provide the essential physical hip protection by cushioning, absorbing and dissipating the fall impact energy while preventing direct contact between the hips 202 (not shown in this drawing, shown in FIGS. 4 and 6) and the ground surface 250 (not shown in this drawing, shown in FIGS. 4, 5, and 7).

FIG. 3*b* is a side cross section view through an airbag 86 schematic illustration of an embodiment of a hip protector system 1 according to the present invention.

In the state shown in the illustration, the airbag 86 is inflated and contains gas 80*a*.

According to some variation of the embodiment pouch 10 is equipped with internal passages for inlaid pneumatic tubules 93 and electrical wires 91.

The side of the pouch designated to be facing the user's body is defined as the internal side 10*i* of the pouch and the opposite side is defined as the external side 10*e* of the pouch.

FIG. 3*c* is a perspective back view schematic illustration of an embodiment of a hip protector system 1 ornamented with a decorative cover 12 according to the present invention.

The pouch 10 is ornamented with an easily mounted and removable decorative cover 12 made of, for example, fabric. The decorative cover 12, according to a variation of the embodiment shown herein, may wrap the pouch 10 without covering the proximity sensors 21. According to a variation of the embodiment shown herein, the decorative cover 12 is closed around the pouch 10 by means of small size fabric hook-and-loop fasteners 12*a* located in a few points along the cover 12. The fasteners may easily be released once the airbags 86 get inflated and pop out of their compartments 10a (not shown in this drawing, shown in FIG. 3a).

FIG. 4 illustrates a wearer 200 standing while wearing a hip protector system 1 according to the present invention.

The airbags 86 (not shown in the present drawing, shown in FIGS. 1, 2b, 3a, 3b, and 5) of which are not inflated and are contained in folded configuration within external compartments 10a, located above the wearer's hips 202, and cannot be seen.

The illustration defines a proximity sensor tilt angle 21a as an angle the origin of which is at the proximity sensor 21 and is measured between the proximity sensor package downward axis 21b and a line 21c perpendicular to the plane 204 of wearer's waist.

The present illustration shows measurements of two proximity sensors 21; one measures the hip to ground surface distance 101 to the ground surface 250, while the other measures the hip distance 101a to an object 260 placed on the ground 250.

The height 102, of the hip 202 above the ground or an object placed on the ground is the vertical component of the distance 101 between a proximity sensor 21 to the ground surface 250.

The shortest height 102a of one of the hips 202 above the ground or an object placed on the ground is presented in the figure as the vertical component of the distance 101a between a proximity sensor 21 to the object 260, in this specific case—a living room table, placed on the ground.

It should be emphasized that, in order to secure wearer compliance, the design of the hip protector system 1 according to the present invention is such that the pouch 10 is conveniently worn, around the wearer's waist 201, like a decorative belt, and no part of it needs to be attached to the wearer's body beneath the waist plane 204 of the wearer.

The pouch 10 is worn over the user's clothing; its circumference is adjustable and it is locked by a one-click buckle in a most simple and convenient way.

FIG. 5 illustrates a wearer 200 lying on the side after having fallen, wearing hip protector system 1 according to the present invention, the airbags 86 of which are inflated.

The large size of the fully deployed airbags 86 protects the femur and in particular the greater trochanter of the femur from direct impact with the ground, by providing a sufficient interspace between the wearer's waist 201 and the ground surface 250, and protects the wearer 200 by absorbing and dissipating the fall impact energy, thus preventing impact injury to the wearer.

The two semi-circled design airbags 86, wrapping the right and left part of the wearer's waist plane 204, in one of the embodiments of the present invention, provide support to the pelvis in a way that could provide protection against other potential fall related fractures and injuries of the pelvis area.

As the present illustration shows, in a fully inflated state of an airbag 86 the airbag inflation size 120, which is the actual distance between the wearer's waist 201 to the ground surface 250, at the instance of the wearer's impact with the ground, is larger than the pelvis to ground surface distance 122.

Proper design and production of the hip protector system ensure that for a wearer 200 of a given weight, at least a predetermined size 120 of the airbag inflation will be achieved.

FIG. 6 illustrates the location of the waist 201, the hip 202, and the pelvis 203 in the human body.

FIG. 7 illustrates a wearer 200, in mid-fall situation, wearing a hip protector system 1 according to the present invention.

The illustration defines hip to ground surface distance 101 as the distance measured between a proximity sensor 21 and the point on the ground surface 250 from which the sensor signal is reflected back, while the height 102 is the vertical component of the hip to ground surface distance 101 between a proximity sensor 21 to the ground surface 250.

The height 102 is calculated based upon the spatial orientation signals received from the gyro 22 (not shown in the present drawing, shown in FIGS. 1, 2a, 3a, and 8).

Likewise, the illustration shows a downward velocity 103, which is the vertical velocity of the pelvis calculated by measurement of the vertical acceleration 107 by the accelerometer 23 (not shown in the present drawing, shown in FIGS. 1, 2a, 3a, and 8). In another way the vertical velocity 103 is calculated based on the change in the height 102 as a function of time.

Figure 8:
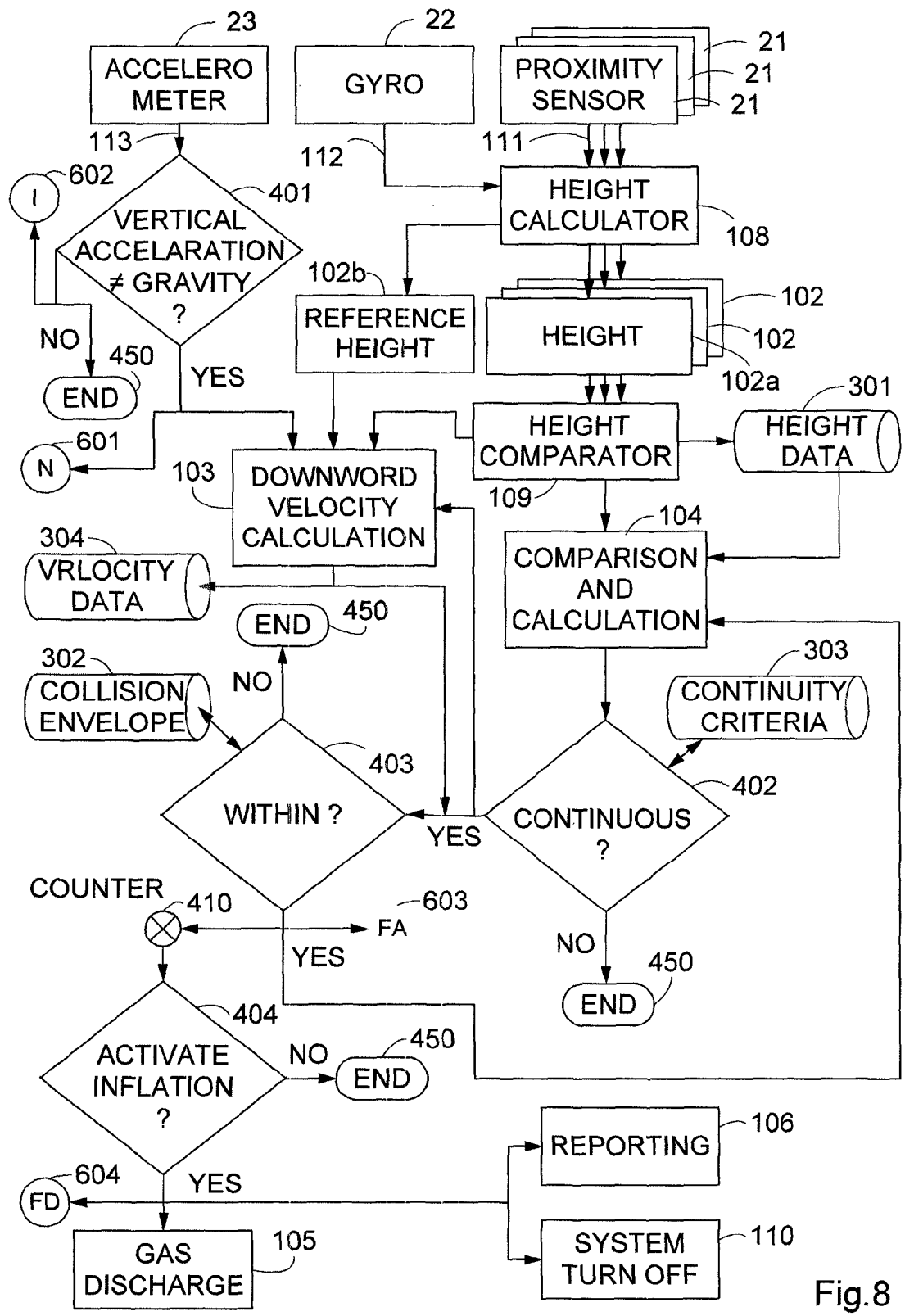
FIG. 8 is a flow chart that schematically illustrates an operation of a hip protector system in accordance with an embodiment of the present invention.

FIG. 8 is a flow chart that schematically illustrates operation of a hip protector system 1 in accordance with an embodiment of the present invention.

Note: for reading convenience, elements are numbered in parentheses here, even though they do not appear in the present flow chart.

Note: any of the following decision making algorithms (401, 402, 403 and 404) that ends up in a decision not to act and denoted by "END", is numbered (450).

Once the main switch (71) is in "on" position and the wearer wears the pouch, the auto operation switch (73) is activated by the locking device (10g) and turns on the hip protector system (1), by connecting the battery (72) to all electricity consuming components (21, 22, 23, 40, 41, 60, 82, and 88) via the power supply bus (50).

Once activated, the system MCU (40) sends a self-test activation signal 115, which initiates an auto self-test procedure, validating the system's physical and logical integrity, the functioning of the sensors, battery power level and gas pressure level.

Once a malfunction is detected, its code appears in the fault display (62) of the status & integrity indicator (60). Faults are announced by an alert sound produced by the warning buzzer (61).

Following malfunction detection, the MCU (40) sends a system malfunction alert signal (116) that triggers the transmission of an alert notification to pre-defined destinations via the auto alert/alarm transmitter (41). The transmission operation may be performed by a destined application stored in the wearer's cell-phone.

The wearer is able to reset the alert sound via the reset button (63), but the system stays non-operative as long as the malfunction has not been handled.

Following a faultless self-test procedure, the buzzer (61) issues a specific readiness sound and the system enters its default "normal" (N) mode of operation (601).

Once the wearer is in a fully stretched standing position, based on height data (102) derived from proximity and spatial orientation measurements, the system records his or her waist height (102) and uses it as a specific reference height value (102b) for further computations (a system parameter associated with the specific wearer). The reference height value (102b) may be updated during the next cycle of hip protector system (1) operation.

System algorithms handle the differences between distance values received from the three proximity sensors (21), which may result, for example, from asymmetrical standing posture as well as, for example, from an object on the ground (260) within the wearer's close vicinity.

The proximity sensors (21) are pointing downwards at a predetermined tilt angle (21a) off the perpendicular to the wearer's waist plane (204), in order to minimize signal reflections from the wearer's body and/or clothing.

The proximity measurement distance signals (111) are transmitted and received at a sampling rate that may change in accordance with the system's mode of operation.

Measurements of hip (202) to ground surface (250) distance (101) and pelvis (203) to ground surface (250) distance (122) are transformed by the MCU (40) height calculator (108) into height values (102), by fusion with spatial orientation signals (112) provided by the system gyro (22).

The calculated height values (102) are transferred to the height comparator (109).

A series of the recently sampled height values (102) for each hip and the pelvis, for a predefined time-slot, is being recorded and stored in the height database 301, for real-time motion trend analysis and for future pre-fall circumstance analysis purposes.

At the same time, a data comparison and calculation (104) of the height change trend is executed, based on height data provided by the height comparator (109) and the recent height data series stored in the height data database (301).

A series of the recently sampled pelvis downward velocity values (103), for a predetermined time-slot, is being recorded and stored in the velocity database 304 for the aforementioned purposes.

System logic assigns higher attention priority to the hip with the shortest height (102a) relative to the ground surface (250) or an object (260) placed on the ground.

Simultaneously, ongoing computations of downward velocity (103) of the pelvis are executed by the MCU (40) via two channels, for cross-check reasons.

The first channel computes the downward velocity (103) based on change of height (102) vs. time.

The second channel computes the downward velocity by utilizing vertical acceleration (107) vs. time data.

In order to avoid false fall alarms and fault system activations, the MCU (40), through its specific set of sensors (21, 22, and 23) and system algorithms, is capable of "filtering" misleading shortest height (102a) measurements that may mistakenly be interpreted as an impending fall situation.

Such false indications may be caused by signal reflections from objects that temporarily block the line of sight between the proximity sensors 21 and the ground surface (250); mainly, from static or moving objects placed on the ground surface or from the wearer's limbs and clothing.

This "filtering" capability is achieved through continuous cross-checks between the reflected signals received from the three proximity sensors (21), as well as by cross-checks of the correlation between the measured changes of hip to ground surface distance (101) and the downward velocity (103) values.

Irregularity in distance measurements is identified by the discontinuity criteria database (303) and serves as another measure of false alarm elimination.

As long as the wearer's hip height (102) is within the range of a standing, walking or transit position, the system stays in "normal" (N) mode of operation (601), no matter the pelvis vertical acceleration (113) value.

As long as the pelvis vertical acceleration (113) data indicates vertical acceleration other than gravity, the system stays in "normal" (N) mode of operation (601), no matter the height (102) values.

At specific combinations of conditions in which both hip height (102) data and vertical acceleration (113) data indicate a continuous motionless situation, at height values typical to seating or lying-down positions, the MCU (40) may issue a command to switch to "idle" (I) mode of operation (602), for battery power saving purpose.

At this sort of "hibernation" mode, the gyro (22) and accelerometer (23) continue their regular operation, while the proximity sensors (21) switch into a reduced level of activity and MCU (40) processing and computation operations are minimized.

As soon as a vertical acceleration other than gravity is identified by the system algorithm asking "vertical acceleration # gravity?" (401), indicating a transition into stand-up position, the MCU (40) issues an immediate command to switch the system back into "normal" (N) mode of operation (601).

As soon as a progression of a likely fall is being identified by the relevant system algorithms asking: "continuous rate of change?" (402) and asking: "within collision envelope?" (403), based on both specific height-velocity sets checked against the collision envelope reference database (302) and height continuity verification against the height continuity criteria reference database (303), the MCU (40) switches the system to "fall alert" (FA) mode of operation (603).

At this mode of operation, the MCU (40) may issue a command to increase data sampling rate, and height-velocity data sets may be checked on a speeded-up basis against the collision envelope reference database (302).

Once a predetermined number of "within collision envelope" (403) data sets are found by the counter and fall trend analyzer (410) to indicate high likelihood of an impending collision with the ground surface (250), an emergency "fall detection" status (FD) (604) is declared by the MCU, and the algorithm asking "activate inflation?" (404) sends an inflation activation signal (114) to the discharge valve (82) of the gas canister (81).

The gas (80a) is speedily discharged through the gas canister outlet (83) and manifold (84) and flows rapidly via the pneumatic tubules (93) and the intake valve (85) into the airbags (86).

As soon as the airbags get inflated, they pop-out of their compartments (10a) and get fully deployed to a size eliminating direct contact between the wearer's hips (202) and the ground surface (250).

Once the wearer (200) collides with the ground surface (250) and the airbags (86) undergo a contraction by the impact, the airbag gas discharge mechanism (87) automatically performs a controlled gas discharge process (105), aimed at enhancing the cushioning effect and avoiding the wearer from being bounced from the ground surface (250) or being trapped between objects in his close proximity.

In parallel to the inflation activation signal (114), the MCU (40) issues a fall-alarm activation signal (117) to the auto alert/alarm transmitter (41), which executes alarm calls/messaging reporting (106) to its pre-programmed destinations.

Following the aforementioned activation procedures, the MCU (40) sends a system turn-off signal (118) to the auto operation switch (73), commanding to turn the system off (110).

During regular use: once the wearer takes off the pouch by pressing the buckle (10h) release mechanism, the MCU (40) turns the system off (110) after a predetermined period of time.

In even further detail, theoretical data-sets resulting in system activation could, for example, be:

TABLE 1

| Data-Set sequential number | Downward velocity [m/s] | Height [m] |
|---|---|---|
| 1 | 0.50 | 0.8 |
| 2 | 1.20 | 0.6 |
| 3 | 1.90 | 0.5 |

These values are in no way limiting the present invention.

Figure 9:
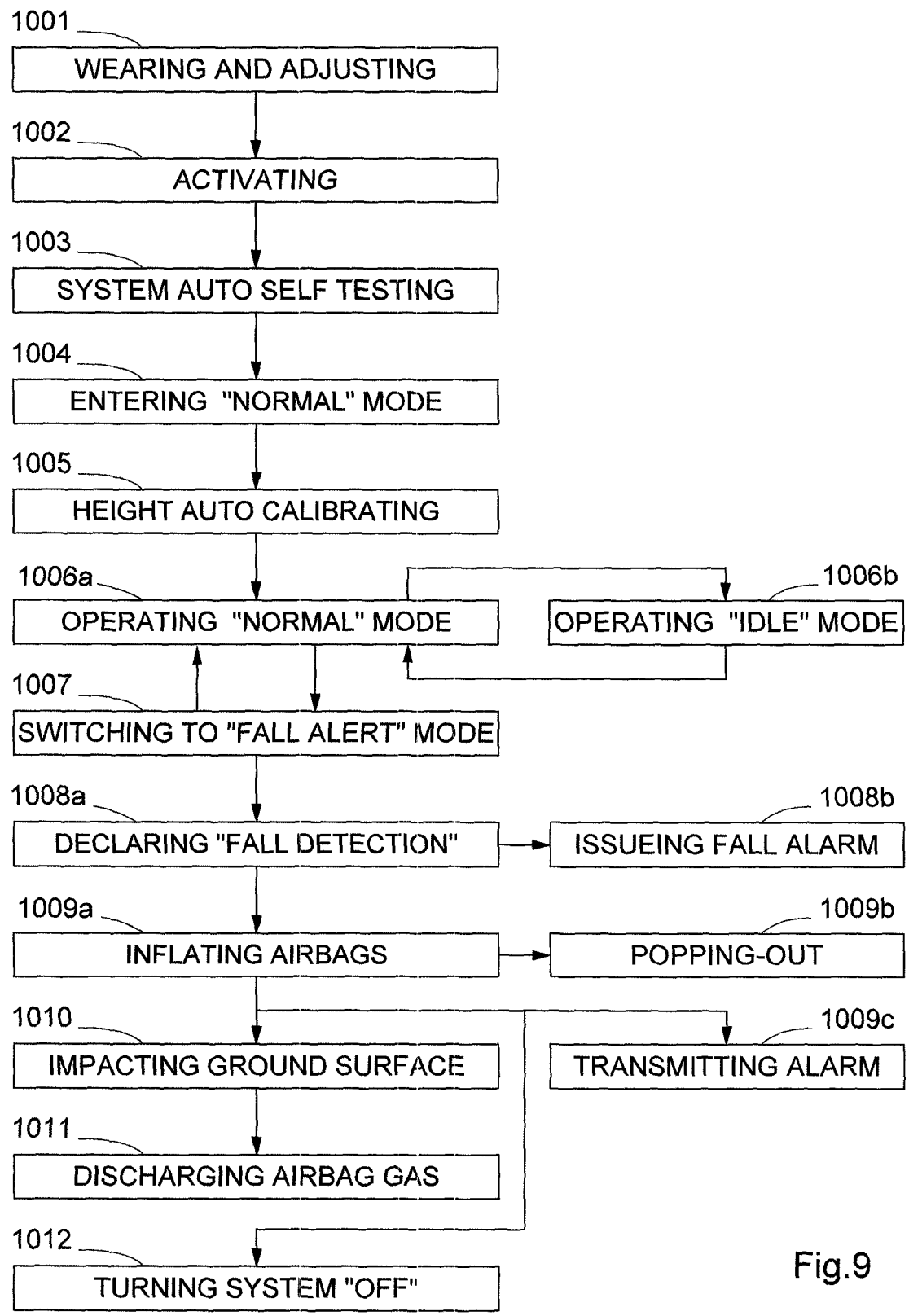
FIG. 9 is a flow chart that schematically illustrates a method of use of a hip protector system in accordance with an embodiment of the present invention.

FIG. 9 is a flow chart that schematically illustrates a method of use of a hip protector system 1 in accordance with an embodiment of the present invention.

Note: for reading convenience, elements are numbered in parentheses here, even though they do not appear in the present flow chart.

The hip protector system (1) is designed and built for fully automated hands-off operation.

Elderly people's limited motor and cognitive skills require simplicity, convenience, and flexibility in operation of the device, in order to secure compliance.

For that reason, the system incorporates a lot of automated functions, which don't require active involvement of the wearer.

The hip protector system's method of use is described hereinafter.

Wearing the pouch (10) by the wearer (200) around his waist (201) and adjusting it to his waist size by using the adjustment clasp (10m) [stage 1001].

Once locking the pouch locking device (10g) while the main switch (72) is in "on" position, the hip protector system (1) is automatically activated by the auto operation switch (73) located in the locking device (10g) [stage 1002].

Following its activation, a system auto-self-testing procedure is performed by the system. If a malfunction is detected, the wearer hears a warning sound produced by the buzzer (61), and he may read the malfunction code presented in the fault display (62) of the status & integrity indicator (60) [stage 1003].

Once a malfunction has been detected, an automatic malfunction alert is being sent to the pre-programmed alert destinations via the system auto alert/alarm transmitter (41), by using, for example, an application stored in the wearer's cell-phone. Such a destination could be a technical support center.

The wearer being able to reset the alarm sound via the reset button (63).

The system stays non-operative as long as the malfunction has not been handled.

Following a faultless auto self-test procedure, the buzzer (61) is issuing a specific readiness confirmation sound and the hip protector system (1) is entering its default "normal" (N) mode of operation (601) [stage 1004].

As soon as the wearer is in a fully stretched standing position, the hip protector system (1) is performing an automatic procedure of waist height re-calibrating [stage 1005].

This procedure enables the fine-tuning of hip protector system (1) parameters (such as response sensitivity) in accordance with the physical attributes of the specific wearer, at a specific point in time, as well as the readjustment of parameters due to usage by more than a single wearer.

EXAMPLE 1

The same wearer is walking barefoot or, in another circumstance, is wearing high-heeled shoes.

EXAMPLE 2

Different patients hospitalized in the same hospital department are using the device alternately.

During routine usage by the wearer, the hip protector system (1) may switch from time to time, without his or her awareness and involvement, from operating "normal" (N) mode [stage 1006a] to operating "idle" (I) mode [stage 1006b] and vice-versa.

In general, the hip protector system (1) stays in N mode as long as the wearer is in standing, walking and transiting positions. The hip protector system (1) stays in I mode following identification of ongoing sitting or lying-down positions.

While in standing, walking or transiting position, as soon as the hip protector system (1) identifies an increased likelihood of an impending fall, it is automatically, switching to "fall alert" (FA) mode of operation [stage 1007].

Assuming that fall progression stops, the system switches back to N mode.

Alternately, if fall progression continues, the hip protector system (1) has the option of switching to "fall detection" (FD) mode of operation.

Following an undoubted identification of a wearer fall progression that is going to end-up in a collision with the ground surface (250), the hip protector system (1) is declaring an emergency "fall detection" situation and performing a series of automated operations intended to minimize impact damage and inform relevant people and authorities on the wearer's fall event [stage 1008a].

The declaring of the emergency "fall detection" situation is accompanied by issuing a fall alarm [stage 1008b].

The hip protector system (1) is issuing a prompt command to inflate the airbags in order to provide effective protection against fall impact and prevent the hips from direct impact with the ground surface, thus—minimizing the likelihood of hip fracture event [stage 1009a].

The inflating airbags popping out of their built-in compartments within a short time interval are cushioning the fall impact as the wearer's waist approaches ground surface [stage 1009b].

In parallel to the airbag inflation activation, the hip protector system (1) is transmitting an automated fall-alarm call/message to pre-programmed destinations, such as family members, caregivers and nursing home staff members [stage 1009c].

Airbag activation report and a maintenance service request message may be transmitted directly to a technical support center.

As soon as the airbags (86) undergo a contraction caused by the impact with the ground surface [stage 1010], the airbag gas discharge mechanism (87) is automatically performing a controlled gas discharging process, aimed at enhancing the cushioning effect and avoiding the wearer from being bounced from the ground surface (250) or being trapped between objects in his or her close proximity [stage 1011].

After a predetermined time, in order to ensure safe recording of pre-fall data required for future fall circumstances analysis, the MCU (40) is sending a system turn-off signal (118) to the auto operation switch (73), which turns off the hip protector system (1) [stage 1012].

Once the system airbags have been inflated, the system becomes inoperative until maintenance activities such as airbag and gas canister replacement have been performed.

The primary advantages of the present invention, compared to known passive hip protectors and/or previous attempts to develop active hip protectors, include the following:

It provides effective physical hip protection against fall impact injury;

It ensures reliable fall detection and minimizes false fall alarms;

It includes height measurements as a key metric used to determine when a real fall is occurring; and It secures wearer compliance through its simple, practical and decorative design, making it easy, attractive and suitable to be worn in almost any indoor and outdoor circumstances.

In conclusion:

Previous attempts to develop fall detection capabilities were typically based on diverse embodiments incorporating sets of accelerometers and tilt sensors, located in different places on the user's body.

Fall detection decisions in these embodiments were supposed to be the outcome of continuous comparison of "normal gait pattern values" (accelerations and tilt angles) to real-time measured values.

The aforementioned method has led to excessively complex system logic and an unacceptable level of system reliability due to false alarms.

The hip protector system's fall detection logic presented herein is avoiding the pitfalls of previous attempts by introducing a completely different fall detection approach, method, and logic.

The system's fall detection logic, according to the present invention, is based on the comparison of real-time values, as measured by the specific set of sensing sensors, with predefined combinations of downward velocity and hip proximity to the ground surface.

This system logic could not be implemented by using a different set of sensors.

Moreover; this fall detection logic may be translated into much simpler algorithms and eliminate false alarms for non-falling events such as, for example, abrupt stooping, sitting, or lying down.

The sensors and the detection logic enable the system to identify "idle situations" during which the system may operate at a lower level of alert. This information is leveraged by switching the system to a low energy consumption mode of operation, which translates into a longer life-time of the system's battery.

The system's disposable components such as battery, airbags and gas canister, may easily be replaced in the field by the wearer, by his or her helpers, or by a technical support staff member.

While the invention has been described with respect to a limited number of embodiments, it will be appreciated that many variations, modifications and other applications of the invention may be made.

For example; different embodiments and variations of the present invention, utilizing the technology and system logic presented above, may be used in the future for protection against fall related damages and injuries typical to human sports and leisure activities, such as: skiing, snowboarding, horse riding, skateboard riding and bicycling.

What is claimed is:

1. A hip protector system configured to be worn around a waist of a user at a waist plane of the user, the hip protector system comprising:

a pouch configured to be worn around a waist of a user, wherein the pouch includes an inflatable airbag;

a plurality of proximity sensors configured to measure a distance from the user's pelvis to a point on the ground surface;

a gyro configured to provide spatial orientation of the waist plane of the user;

an accelerometer configured to determine the vertical acceleration of the waist plane of the user;

a micro controller unit operatively connected to said proximity sensors, said gyro, and said accelerometer; wherein the micro controller unit is configured to:

receive a vertical acceleration direction from the accelerometer;

receive proximity measurement distance signals respectively, from the proximity sensors;

receive or compute spatial orientation relative to the vertical direction based on signals provided by the gyro;

calculate heights respectively based on said proximity measurement distance signals and said spatial orientation signals;

transfer said calculated heights to a height comparator for comparing respective calculated height values from the proximity sensors;

filter out shortest height measurements caused by signal reflections from objects that temporarily block the line of sight between at least one of the proximity sensors and the ground surface to determine a true height from the waist plane of the user to the ground surface; and wherein the airbag is inflated responsive to the true height from the waist plane of the user to the ground surface to protect the user.

2. The hip protector system of claim 1, wherein the inflatable airbag includes a first airbag and a second airbag, wherein the first airbag is configured to be wrapped against the right part of the waist of the user, and the second airbag is configured to be wrapped against the left part of the waist of the user.

3. The hip protector system of claim 1, further comprising:

a pneumatic sub-system to inflate the airbag by discharging compressed gas into the airbag upon detection of a fall event.

4. The hip protector system of claim 1, wherein the micro controller unit is further configured to:

compute a first value of downward velocity based on a change of the true height in time;

compute a second value of downward velocity based on the vertical acceleration in time;

and correlate the first value of downward velocity and the second value of downward velocity to validate the true height in time from the waist plane of the user to the ground surface.

5. The hip protector system of claim 4, wherein the micro controller unit is further configured to:

identify irregularity in the user's pelvis to ground surface distance measurements based on a discontinuity criteria database.

6. The hip protector system of claim 5, wherein the micro controller unit is configured to:

detect a fall event by checking height-velocity sets of values against a collision envelope reference database and by verifying continuity of the height against a height continuity criteria reference database, wherein a fall event is detected if the continuity is verified and a predetermined number of within-collision-envelope height-velocity sets are found.

7. The hip protector system of claim 6, further comprising:
   a pneumatic sub-system configured to inflate the airbag by discharging compressed gas into the airbag, wherein the micro controller unit is configured to:
   activate the pneumatic sub-system upon detection of a fall event.

8. The hip protector system of claim 7, further comprising:
   gas discharge mechanism configured to perform a controlled gas discharging process when the airbag undergoes a contraction caused by an impact with a ground surface.

9. A method for hip protection by use of a hip protector system including: a pouch configured to be worn around a waist of a user, wherein the pouch includes an inflatable airbag, a plurality of proximity sensors configured to measure a distance from the user's pelvis to a point on the ground surface, a gyro, an accelerometer and a micro controller unit operatively connected to the proximity sensors, the gyro, and the accelerometer, the method comprising:
   receiving a vertical acceleration direction from the accelerometer;
   receiving distance signals respectively from the proximity sensors;
   receiving or computing spatial orientation relative to the vertical direction based on signals provided by the gyro;
   calculating heights respectively based on said distance signals and said spatial orientation signals; and
   filtering out shortest height caused by signal reflections from objects that temporarily block the line of sight between at least one of the proximity sensors and the ground surface thereby determining a true height from the waist plane of the user to the ground surface;
   wherein the airbag is inflated responsive to the true height from the waist plane of the user to the ground surface to protect the user.

10. The method for hip protection of claim 9, wherein the inflatable airbag includes a first airbag and a second airbag, wherein the first airbag is configured to wrap against the right part of the waist of the user, and the second airbag is configured to wrap against the left part of the waist of the user.

11. The method for hip protection of claim 9, further comprising:
   computing a first value of downward velocity based on a change of the true height in time;
   computing a second value of downward velocity based on the vertical acceleration in time; and correlating the first value of
   downward velocity and the second value of downward velocity to validate the true height from the waist plane of the user to the ground surface.

12. The method for hip protection of claim 9, further comprising:
   identifying irregularity in the user's pelvis to ground surface distance measurements based on a discontinuity criteria database.

13. The method for hip protection of claim 9, further comprising:
   checking height-velocity sets of values against a collision envelope reference database;
   verifying continuity of the height against a height continuity criteria reference database; and
   detecting a fall event if the continuity is verified and a predetermined number of within-collision-envelope height-velocity sets are found.

14. The method for hip protection of claim 9, further comprising:
   activating a pneumatic sub-system upon detection of a fall event; and
   inflating an airbag by discharging compressed gas into the airbag by the pneumatic sub-system.

15. The method for hip protection of claim 14, further comprising:
   performing a controlled gas discharging process when the airbag undergoes a contraction caused by an impact with a ground surface.

* * * * *